(12) United States Patent
Kern

(10) Patent No.: US 11,806,377 B2
(45) Date of Patent: Nov. 7, 2023

(54) ORAL USE OF CORIANDER SEED OIL FOR A SOOTHING EFFECT ON REACTIVE SKIN

(71) Applicant: Societe d'Exploitation de Produits Pour les Industries Chimiques Seppic, Paris (FR)

(72) Inventor: Catherine Kern, Paris (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 10 days.

(21) Appl. No.: 17/052,391

(22) PCT Filed: May 2, 2019

(86) PCT No.: PCT/FR2019/051011
§ 371 (c)(1),
(2) Date: Nov. 2, 2020

(87) PCT Pub. No.: WO2019/211562
PCT Pub. Date: Nov. 7, 2019

(65) Prior Publication Data
US 2021/0085740 A1    Mar. 25, 2021

(30) Foreign Application Priority Data
May 4, 2018   (FR) ...................................... 1853879

(51) Int. Cl.
| | | |
|---|---|---|
| *A61K 36/23* | (2006.01) |
| *A23L 33/24* | (2016.01) |
| *A23L 33/18* | (2016.01) |
| *A23L 33/00* | (2016.01) |
| *A23L 29/262* | (2016.01) |
| *A23L 33/175* | (2016.01) |
| *A23L 29/00* | (2016.01) |
| *A23L 29/30* | (2016.01) |
| *A23L 33/105* | (2016.01) |
| *A23L 33/115* | (2016.01) |
| *A23L 29/212* | (2016.01) |
| *A23L 33/15* | (2016.01) |
| *A23L 33/135* | (2016.01) |
| *A61K 9/14* | (2006.01) |
| *A61K 9/28* | (2006.01) |
| *A61K 9/48* | (2006.01) |
| *A61K 47/02* | (2006.01) |
| *A61K 47/08* | (2006.01) |
| *A61K 47/18* | (2017.01) |
| *A61K 47/22* | (2006.01) |
| *A61K 47/26* | (2006.01) |
| *A61K 47/38* | (2006.01) |
| *A61K 47/42* | (2017.01) |
| *A61K 47/44* | (2017.01) |
| *A61K 47/46* | (2006.01) |

(52) U.S. Cl.
CPC ............ *A61K 36/23* (2013.01); *A23L 29/015* (2016.08); *A23L 29/04* (2016.08); *A23L 29/045* (2016.08); *A23L 29/212* (2016.08); *A23L 29/262* (2016.08); *A23L 29/30* (2016.08); *A23L 33/105* (2016.08); *A23L 33/115* (2016.08); *A23L 33/135* (2016.08); *A23L 33/15* (2016.08); *A23L 33/175* (2016.08); *A23L 33/18* (2016.08); *A23L 33/24* (2016.08); *A23L 33/30* (2016.08); *A61K 9/14* (2013.01); *A61K 9/28* (2013.01); *A61K 9/4808* (2013.01); *A61K 47/02* (2013.01); *A61K 47/08* (2013.01); *A61K 47/183* (2013.01); *A61K 47/18* (2013.01); *A61K 47/22* (2013.01); *A61K 47/26* (2013.01); *A61K 47/38* (2013.01); *A61K 47/42* (2013.01); *A61K 47/44* (2013.01); *A61K 47/46* (2013.01); *A61K 2800/92* (2013.01)

(58) Field of Classification Search
CPC . A61K 36/23; A61K 9/14; A61K 9/28; A61K 9/48; A61K 47/02; A61K 47/08; A61K 47/18; A61K 47/22; A23L 33/24; A23L 33/18; A23L 33/00; A23L 29/262; A23L 33/175; A23L 29/00; A23L 29/30; A23L 33/105; A23L 33/115; A23L 33/212; A23L 33/15; A23L 33/135
See application file for complete search history.

(56) References Cited

U.S. PATENT DOCUMENTS

| | | |
|---|---|---|
| 6,365,175 B1 | 4/2002 | Alaluf et al. |
| 6,440,434 B1 | 8/2002 | Barrett et al. |

FOREIGN PATENT DOCUMENTS

| | | |
|---|---|---|
| CN | 1365272 A | 8/2002 |
| EP | 0709084 A2 | 5/1996 |
| EP | 0888773 A1 | 1/1999 |
| EP | 1932510 A1 | 6/2008 |
| EP | 1932510 B1 * | 6/2008 |
| WO | 99/02149 A1 | 1/1999 |
| WO | 2014181267 A1 | 11/2014 |

OTHER PUBLICATIONS

Duarte et al. An Bras Dermatol. 2017;92(4):521-525.*

(Continued)

*Primary Examiner* — Shirley V Gembeh
(74) *Attorney, Agent, or Firm* — NIXON & VANDERHYE

(57) ABSTRACT

An oil from seeds of at least one umbelliferous plant, coriander, in ingestible form for preventing or slowing the appearance of dysesthetic sensations on sensitive human skin.

13 Claims, No Drawings

(56) References Cited

OTHER PUBLICATIONS

EFSA journal 2013; 11(10):3422.*
Office Action issued in Chinese Patent Application No. 201980029691.9 dated Jul. 29, 2022.
Yadav and Chaudhary, "Cosmeceutical assets of ancient and contemporary ayurvedic astuteness," International Journal of Green Pharmacy, 2015, vol. 9, No. 4, pp. S1-S6.
Prachayasittikul et al., "Coriander (Coriandrum sativum): A promising functional food toward the well-being," Food Research International, 2018, vol. 105, pp. 305-323.
Reuter et al., "Anti-inflammatory potential of a lipolotion containing coriander oil in the ultraviolet erythema test," Original Article, Journal of the German Society of Dermatology, 2008, vol. 6, pp. 847-851.
Ammar et al., "Study of The Anti-Inflammatory Activity of Some Medicinal Edible Plants Growing in Egypt," Journal of Islamic Academy of Sciences, 1997, vol. 10, No. 4, pp. 113-122.
Attia et al., "Characterization of antiradical and anti-inflammatory activities of some cold pressed oils in carrageenan-induced rat model of acute inflammation," Der Pharma Chemica, 2016, vol. 8, No. 17, pp. 148-158.
Ibrahim et al., "Biochemical characterization, anti-inflammatory properties and ulcerogenic traits of some cold pressed oils in experimental animals," Pharmacetical Biology, 2017, vol. 55, No. 1, pp. 740-748.
Zhang et al., "Evaluation of coriander spice as a functional food by using in vitro bioassays," Food Chemistry, 2015, vol. 167, pp. 24-29.

* cited by examiner

ORAL USE OF CORIANDER SEED OIL FOR A SOOTHING EFFECT ON REACTIVE SKIN

The present invention relates to the use of at least one oil from seeds of an umbelliferous plant for preventing or slowing the appearance of dysesthetic sensations on sensitive human skin.

The skin is the body's first protective barrier against the environment. It is therefore subject to numerous external attacks which can lead to uncomfortable cutaneous reactions or even, in the case of very intense or more serious reactions, to phenomena of cutaneous irritation and/or inflammation. Uncomfortable cutaneous reactions may in particular be induced by contact with chemical products such as cleaning agents, perms, hair colorings, or result from mechanical actions such as shaving, scrubbing, peeling, epilation, or result from the action of temperature, climate, ultraviolet radiation or even atmospheric pollution.

Sensitive or reactive skin is more particularly vulnerable to the consequences of these external attacks. Sensitive or reactive skin is a condition which affects many people: approximately 50% of people (60% of women, 40% of men) report having reactive skin. It was recently defined as "a syndrome defined by the occurrence of unpleasant sensations (stinging, burning, pain, pruritus, and tingling sensations) in response to stimuli that normally should not provoke such sensations. These sensations cannot be explained by lesions attributable to any skin disease. The skin can appear normal or be accompanied by erythema. Sensitive skin can affect all body locations, especially the face" (1).

Environmental factors such as exposure to ultraviolet radiation, air pollution, climate (hot, cold, wind), or lifestyle (food or cosmetic habits), or physiological factors such as stress, endogenous hormones, have been recognized as potentially inducing or aggravating the symptoms of sensitive skin (2). Two main reasons may explain the symptoms of sensitive skin: first, an increase in the permeability of the stratum corneum, and secondly an acceleration of nerve responses (3).

Indeed, several studies have demonstrated a link between sensitive skin and disruption to the barrier function, resulting in the perception of skin discomfort. Degradation of the barrier function has also been associated with atopic dermatitis and it has been shown that persons with sensitive skin have an increased incidence of atopy and a higher risk of developing allergies. Lastly, persons suffering from atopic dermatitis report having sensitive skin, with 80% of them reporting it to be moderate to very sensitive. These data suggest the possible existence of a link between atopic dermatitis and sensitive skin (2).

In addition, in the light of the sensations described in sensitive skin, it is highly likely that sensitive skin exhibits a neurosensory dysfunction, whether this be that the nerve endings at the surface of the skin are less protected because of the degradation of the cutaneous barrier, or that they are hyper-reactive. The cutaneous nerve fibers such as the unmyelinated C fibers induce, inter alia, sensations of pain and itching, and bear on their surface sensory neuroreceptors such as TRP (transient receptor potential) channels, which are known for inducing sensations of pain, burning and itching in sensitive skin (3).

In particular, TRPA1 (transient receptor potential ankyrin 1) is a nociceptor channel which is present on the surface of C fibers and also of keratinocytes, melanocytes and fibroblasts and which may be activated by a certain number of exogenous factors (low temperatures, components of mustard oil—including AITC or allyl isothiocyanate, environmental pollutants, certain pruritogenic agents, etc.) and endogenous factors (reactive oxygen species, nitrogen monoxide, lipid oxidation products). It is also under the control of intracellular sensitization processes involving several inflammatory mediators such as growth factors, bradykinins, certain proteases, and cytokines (4).

TRPA1 is involved in a certain number of physiological and cellular processes in humans, including nociception, especially in response to chemical irritants, itching/pruritus, neurogenic inflammation and thermosensation (5). For example, TRPA1 is involved in the transmission of histamine-independent itching sensations to the central nervous system. The expression of TRPA1 in nerve endings is higher in the lesions of patients suffering from atopic dermatitis. TRPA1 has also been implicated in the itching/scratching cycles provoked in dry skin, which is consistent with the fact that TRPA1 is an essential sensor of attacks on the cutaneous barrier (6).

The appearance of signs of discomfort within the minutes following contact of the subject with the triggering element is one of the essential characteristics of sensitive skin exhibiting a neurosensory dysfunction.

These signs of discomfort are primarily dysesthetic sensations. "Dysesthetic sensations" are understood to mean more or less painful sensations felt in a cutaneous area such as prickling, tingling, itching, burning, hotness, discomfort, tightness.

Cosmetic and/or dermatological and/or nutritional compositions which can be used for preventing or slowing the appearance of dysesthetic sensations on sensitive skin, and more particularly prickling, tingling, itching, tightness, may be administered orally or topically. They generally comprise fatty phases consisting of at least one oil of plant, animal, mineral or synthetic origin. Among these oils, vegetable oils are widely used because the market trend is oriented toward the use of products derived from the natural world.

Vegetable oils mainly consist of triglycerides, which are distinguished by various natures of the fatty chains and which, after glycerolysis, make it possible to access a characteristic distribution of fatty carboxylic acids.

Vegetable oils are therefore differentiated from vegetable essential oils since essential oils are fragrant products obtained from plant material, generally by steam distillation. An essential oil extracted from a plant therefore cannot contain fatty triglycerides.

Among these fatty carboxylic acids present in the form of triglycerides in the vegetable oils, petroselinic acid or (Z)-octadec-6-enoic acid is known for its use in the treatment or prophylaxis of skin or scalp diseases. The international patent application published under the number WO 99/02149 A1 describes in particular its use against psoriasis-related inflammation, erythema (sunburn), eczema, seborrheic dermatitis, alopecia areata, mycosis, acne or other dermatoses, for example. The applications may also be extended to inflammations of the eye (inflammation of the cornea) and of the mucous membranes, in particular of the oral, nasal, buccal and vaginal mucous membranes. The international patent application published under the number WO 99/02149 A1 also describes that a composition comprising petroselinic acid can be administered orally so that the petroselinic acid can act on the mucous membranes (the buccal, esophageal, stomach and intestinal mucous membranes), and/or that it can pass into the bloodstream and be delivered directly to the skin, eye or mucous membrane cells.

Petroselinic acid is more particularly present in oils originating from an umbellifer, a plant the flowers of which are arranged in umbels.

In the field of cosmetics, coriander has been used as an ingredient in the traditional Ayurvedic cosmetic formula (Varnakarlepa) in order to normalize the color of the skin (7). On the other hand, the effects described relate to the essential oil of coriander and not the oil of coriander seeds (8).

The effects of coriander are known and more particularly on the skin: the essential oil of coriander is described for its inflammatory effects (9).

A powder from coriander seeds has shown an anti-inflammatory effect in vivo in an inflammatory model of edema induced by injection of carrageenans in rats (10). While coriander oil has shown a free-radical scavenging effect in tubo, it has not shown an anti-inflammatory effect in the same in vivo model as above (11).

According to the same study model, coriander oil did not make it possible to reduce paw edema in rats (12).

Coriander extracts, obtained by extraction with hexane or methanol, have shown in vitro activity on the inhibition of the enzymes cyclooxygenase-1 and -2 (13). However, the signalling pathways involved between cyclooxygenases/lipoxygenases on the one hand and the activation of sensory neurons on the other are not correlated, and no effect on the sensations of itching, pruritus or discomfort have been observed or demonstrated.

The European patent application published under the number EP0888773 A1 relates to the use of petroselinic acid for the treatment of inflammation of the superficial tissues, in particular for the preparation of a composition intended to activate the peroxisomal β-oxidation of fatty acids in the superficial tissues of a mammal so as to be able to treat or prevent inflammations and/or modulate lipid metabolism of the superficial tissues has been abandoned due to a prior art which has been judged to be too large. However, nothing in EP0888773 A1 describes the use of coriander seed oil for preventing and/or reducing the sensations of discomfort resulting from sensitive or reactive skin, and in particular the sensations of itching, pruritus, prickling, tingling, itching, or tightness.

The American patent published under the number U.S. Pat. No. 6,365,175 relates to the use of petroselinic acid in the food sector, and in particular for preparing food supplement compositions used as anti-inflammatory compositions which inhibit the production of arachidonic acid metabolites and/or reduce the formation of intracellular adhesion molecules, or as anti-aging compositions. Yet nothing in U.S. Pat. No. 6,365,175 discloses or teaches the use of coriander seed oil for preventing and/or reducing the sensations of discomfort resulting from sensitive or reactive skin, and in particular the sensations of itching, pruritus, prickling, tingling, itching, or tightness.

Within the scope of their research concerning the treatment of dysesthetic sensations in sensitive human skin, the inventor endeavored to develop a novel composition having positive effects on sensitive skin.

In a first aspect, the invention provides a use of at least one oil from seeds of at least one umbelliferous plant as an ingestible cosmetic active principle for preventing or slowing the appearance of dysesthetic sensations on sensitive human skin.

"Dysesthetic sensations" are understood within the context of the present application to mean sensations felt in a cutaneous area such as prickling, tingling, itching, burning, hotness, or tightness.

The oils from seeds of such umbelliferous plants are obtained by implementing a process comprising at least one step of grinding the seeds and/or at least one step of pressing the seeds, and at least one subsequent step of refining the oily liquid obtained after the grinding and/or pressing step.

Preference is given to preferably using coriander seed oil.

Depending on the case, the use according to the invention may have one or more of the following features:

the umbelliferous plant is chosen from coriander, chervil, celery, cumin, carrot, dill, parsley and fennel, the umbelliferous plant is coriander, the oil from seeds of an umbelliferous plant comprises, per 100% of its weight, a proportion by weight of at least one triglyceride of greater than or equal to 99%, the triglyceride being a compound of formula (I):

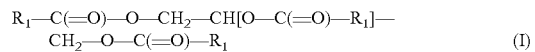

$$R_1-C(=O)-O-CH_2-CH[O-C(=O)-R_1]-CH_2-O-C(=O)-R_1 \quad (I)$$

where $R_1-C(=O)-$ is an acyl radical selected from members of the group consisting of the radicals palmitoyl (or hexadecanoyl), stearoyl (or octadecanoyl), petroselinoyl (or (Z)-octadec-6-enoyl), oleyl (or cis-octadec-9-enoyl), and linoleoyl (or cis, cis-9,12-octadecadienoyl), linolenoyl (or (9Z,12Z,15Z)-9,12,15-octadecatrienoyl), the oil from seeds of an umbelliferous plant comprises, per 100% of the weight of triglycerides of formula (I), an amount by weight of between 40% and 85%, and more particularly of between 55% and 80%, and more particularly still of between 60% and 75%, of a triglyceride of formula (I) for which the radical $R_1C(=O)-$ is the petroselinoyl (or (Z)-octadec-6-enoyl) radical, the oil from seeds of an umbelliferous plant comprises, per 100% of the weight of triglycerides of formula (I), an amount by weight of between 2% and 5% of a triglyceride of formula (I) for which the radical $R_1C(=O)-$ is the palmitoyl radical, and/or an amount by weight of between 0% and 1.5% of a triglyceride of formula (I) for which the radical $R_1C(=O)-$ is the stearoyl radical, and/or an amount by weight of between 60% and 75% of a triglyceride of formula (I) for which the radical $R_1C(=O)-$ is the petroselinoyl (or (Z)-octadec-6-enoyl) radical, and/or an amount by weight of between 8% and 15% of a triglyceride of formula (I) for which the radical $R_1C(=O)-$ is the oleyl radical, and/or an amount by weight of between 12% and 19% of a triglyceride of formula (I) for which the radical $R_1C(=O)-$ is the linoleoyl radical, and/or an amount by weight of between 0% and 1% of a triglyceride of formula (I) for which the radical $R_1C(=O)-$ is the linolenoyl radical.

A subject of the present invention is also an edible composition ($C_A$) comprising, per 100% of its weight:

from 1% to 90% of at least one oil from seeds of an umbelliferous plant as defined previously, and from 10% to 99% of at least one edible technological additive.

"Edible technological additive" denotes any chemical substance or any chemical composition the technical function of which is to enable and/or to facilitate the mixing of different constituents of said composition (CA), to facilitate and/or to optimize the physical properties of said composition (CA), such as for example to facilitate and/or to optimize its flow, its stability, and its incorporation into a subsequent pharmaceutical and/or nutritional formulation, and which is able to meet the conditions required by the regulations in force for the marketing of a pharmaceutical formulation and/or of a nutritional formulation.

Depending on the case, the composition ($C_A$) according to the invention may have one or more of the following features:
- the edible technological additive is a diluent, a flow agent, a binder or a disintegrating agent,
- the diluent is chosen from lactose, sucrose, saccharose, glucose, maltodextrin, mannitol, sorbitol, xylitol, isomalt, calcium hydrogen phosphate, microcrystalline cellulose, starches and more particularly corn starches, wheat starches, potato starches, dicalcium phosphate, anhydrous dibasic calcium phosphate, sodium carbonate, calcium carbonate and magnesium carbonate, monoglycerides and/or diglycerides of fatty acids comprising from 8 to 24 carbon atoms,
- the flow agent is chosen from magnesium stearate, talc, sodium stearyl fumarate, hydrogenated vegetable oils, anhydrous colloidal silica, sodium benzoate and silica dioxide,
- the binder is chosen from starches in the form of starch paste, pregelatinized starches, hydroxypropyl methyl cellulose, methyl cellulose, sucrose syrups and acacia gum,
- the disintegrating agent is chosen from starches, sodium starch glycolate, alginic acid, sodium alginate, sodium croscarmellose, crospovidone, polyvinylpyrrolidone.

The composition ($C_A$) which is a subject of the present invention may be in any physical form, and more particularly in the form of a powder.

When the composition ($C_A$) is in the form of a tablet, it preferably comprises:
- from 50 mg to 200 mg of the oil from seeds of at least one umbelliferous plant for a 500 mg tablet,
- from 100 mg to 400 mg of the oil from seeds of at least one umbelliferous plant for a 1000 mg tablet.

When the composition ($C_A$) is in the form of a soft capsule, it preferably comprises:
- from 800 mg to 1100 mg of the oil from seeds of at least one umbelliferous plant for a 1200 mg soft capsule.

When the composition ($C_A$) is in the form of a hard capsule, it preferably comprises:
- from 3 mg to 50 mg of the oil from seeds of at least one umbelliferous plant for a 100 mg hard capsule,
- from 30 mg to 100 mg of the oil from seeds of at least one umbelliferous plant for a 1000 mg hard capsule.

When the composition ($C_A$) is in the form of a powder, it preferably comprises:
- from 200 mg to 600 mg of the oil from seeds of at least one umbelliferous plant for a powder of 2000 mg,
- from 100 mg to 300 mg of the oil from seeds of at least one umbelliferous plant for a powder of 20 g.

When the composition ($C_A$) is in the form of a powder, it is obtained by introducing its various constituents into a mixer equipped with at least one mechanical stirring system, such as for example flat or impeller-type stirring blades, and the mixer is optionally a tumbler mixer, and the mixer is optionally equipped with a lump breaker system. This mixing operation is generally carried out at ambient temperature.

When the composition (CA) is in the form of a confectionery gum, it preferably comprises:
- from 300 mg to 500 mg of the oil from seeds of at least one umbelliferous plant for a 1.5 mg confectionery gum,
- from 100 mg to 300 mg of the oil from seeds of at least one umbelliferous plant for a 10 g confectionery gum.

When the composition ($C_A$) is in the form of a liquid, it preferably comprises:
- from 300 mg to 500 mg of the oil from seeds of at least one umbelliferous plant for a 1 ml ampoule,
- from 100 mg to 300 mg of the oil from seeds of at least one umbelliferous plant for a 1.5 l bottle.

A subject of the present invention is also a food supplement making it possible to prevent or slow the appearance of dysesthetic sensations on sensitive human skin and comprising an edible composition ($C_A$) according to the invention.

"Food supplement" is understood to mean a foodstuff the purpose of which is to supplement the normal diet and which constitutes a concentrated source of nutrients or other substances having a nutritional or physiological effect alone or in combination. The food supplement makes it possible to prevent certain deficiencies or to respond to specific needs in the diet of an individual, in particular during physical exertion. This definition of "food supplement" is given in Article 2 of Decree No. 2006-352 of Mar. 26, 2006, of the French Republic concerning food supplements and in Directive 2002/46/EC of the European Parliament and of the Council of Jun. 10, 2002.

Preferably, the food supplement according to the invention may have one or more of the following features:
- it is in solid or liquid form,
- it is in solid form and takes the form of a tablet, a hard capsule, a soft capsule, a powder, a sugar-coated tablet or granules,
- it comprises, per 100% of its weight, from 5% to 70% by weight, more particularly from 10% to 70% by weight, and more particularly still from 25% to 70% by weight, of the edible composition ($C_A$),
- it comprises at least one active principle chosen from bioactive lipids, water-soluble or water-dispersible trace element salts, water-soluble or liposoluble vitamins, prebiotics, probiotics, milk proteins and/or milk protein concentrates, plant or animal enzymes, amino acids, peptides, sugars, flavor enhancers and flavoring agents.

The dry forms used in the industries of human or veterinary pharmaceuticals, and of food supplements, are generally provided in the form of tablets, hard capsules, sugar-coated tablets, granules, which are made by agglomeration of solid particles comprising at least one active principle and/or at least one nutritional ingredient and at least one excipient. These dry forms can be prepared by the implementation of many techniques known to a person skilled in the art, such as, for example, compression, pelletization, granulation, compacting or extrusion techniques.

When the food supplement according to the invention is in the form of a powder, it is obtained by introducing its various constituents into a mixer equipped with at least one mechanical stirring system, such as for example flat or impeller-type stirring blades, and the mixer is optionally a tumbler mixer, and the mixer is optionally equipped with a lump breaker system. This mixing operation is generally carried out at ambient temperature.

The food supplement may be in any form of food product known to a person skilled in the art, such as a drink, and more particularly an aqueous drink, a solution, a fruit juice, a flavored drink, an energy drink, an alcoholic drink, a coffee-based drink, a chocolate-based drink, a tea-based drink, a milk product, and more particularly milk, yoghurt, a milk desert, drinkable yoghurt, a cheese, an ice cream, a chocolate bar, a cereal product, and more particularly a cereal bar, a cookie, breakfast cereal, flours, bread making products, a specialized nutrition product, more particularly an infant nutrition product, a nutrition product to prepare for physical exertion, a clinical nutrition product, a meal substitute, candies, more particularly chewing gums, sweets, caramels, dragées, lozenges, marshmallows, Turkish delight, nougats, fruit jellies, liquorice.

The food supplement according to the invention may also be in any presentation form known to a person skilled in the art, such as for example in the form of a tablet, a hard capsule, a soft capsule, a syrup, a powder, such as for example an immediate-release powder, a delayed-release powder or a powder for reconstituted drinks, a liquid, a stick, or a gel.

In general, as mentioned above, the food supplement which is a subject of the present invention may also comprise at least one active principle chosen from bioactive lipids, water-soluble or water-dispersible trace element salts, water-soluble or liposoluble vitamins, prebiotics, probiotics, milk proteins and/or milk protein concentrates, plant or animal enzymes, amino acids, peptides, sugars, flavor enhancers and flavoring agents.

As bioactive lipids optionally present in the food supplement which is a subject of the present invention, mention may be made of phytosterols, such as those extracted from vegetable oils, and more particularly extracts of sea-buckthorn oil, corn oil or soybean oil; phytosterol complexes, isolated from vegetable oils, such as, for example, cholestatin, composed of campesterol, stigmasterol and brassicasterol; phytostanols; carotenoids, which belong to the family of the terpenoids, extracted from algae, green plants, fungi or bacteria; polyunsaturated fatty acids of the omega-3 group, such as, for example, α-linolenic acid, eicosapentaenoic acid or docosahexanoic acid; polyunsaturated fatty acids of the omega-6 group, such as, for example, linoleic acid, γ-linolenic acid, eicosadienoic acid, dihomo-γ-linolenic acid, arachidonic acid, docosadienoic acid, docosatetraenoic acid or docosapentaenoic acid.

As examples of water-soluble or water-dispersible trace element salts optionally present in the food supplement which is a subject of the present invention, mention may be made of ferrous carbonate, ferrous chloride tetrahydrate, ferric chloride hexahydrate, ferrous citrate hexahydrate, ferrous fumarate, ferrous lactate tetrahydrate, ferrous sulfate monohydrate, ferrous sulfate heptahydrate, ferrous chelate of amino acid hydrates, iron glycine chelate; calcium iodate hexahydrate, anhydrous calcium iodate; sodium iodide, potassium iodide; cobalt acetate tetrahydrate, basic cobalt carbonate monohydrate, cobalt carbonate hexahydrate, cobalt sulfate heptahydrate, cobalt sulfate monohydrate, cobalt nitrate hexahydrate; cupric acetate monohydrate, basic copper carbonate monohydrate, cupric chloride dihydrate, copper methionate, cupric sulfate pentahydrate, cuprous chelate of amino acid hydrates, cuprous chelate of glycine hydrate, copper chelate of hydroxy analog of methionine; manganous carbonate, manganous chloride tetrahydrate, manganese hydrogen phosphate trihydrate, manganous sulfate tetrahydrate, manganous sulfate monohydrate, manganese chelate of amino acids hydrate, manganese chelate of glycine hydrate, manganese chelate of hydroxy analog of methionine; ammonium molybdate, sodium molybdate, sodium selenite, sodium selenate; the organic form of selenium produced by *Saccharomyces cerevisiae*, selenomethionine (inactivated selenium yeast), and the selenomethionine produced by *Saccharomyces cerevisiae* (inactivated selenium yeast).

As examples of water-soluble or liposoluble vitamins optionally present in the food supplement which is a subject of the present invention, mention may be made of: vitamin A, more particularly in its form of retinol, retinyl acetate, retinyl palmitate or β-carotene; vitamin D2, more particularly in its form of ergocalciferol or 25-hydroxycalciferol, vitamin D3, more particularly in its form of cholecalciferol, vitamin K, more particularly in its form of phylloquinone (phytomenadione) or menaquinone, vitamin B1, more particularly in its form of thiamine hydrochloride, thiamine mononitrate, thiamine monophosphate chloride or thiamine pyrophosphate chloride, vitamin B2, more particularly in its form of riboflavin or riboflavin 5'-phosphate sodium, vitamin B6, more particularly in its form of pyridoxine hydrochloride, pyridoxine 5'-phosphate or pyridoxal 5'-phosphate, vitamin B12, more particularly in its form of cyanocobalamin, hydroxocobalamin, 5'-deoxyadenosylcobalamin or methylcobalamin, vitamin C, more particularly in its form of L-ascorbic acid, sodium L-ascorbate, calcium L-ascorbate, potassium L-ascorbate, calcium salts of 6-palmitoyl-L-ascorbic acid or sodium ascorbyl monophosphate, pantothenic acid, more particularly in its form of calcium D-pantothenate, sodium D-pantothenate, dexpanthenol or pantethine, vitamin PP, more particularly in its form of nicotinic acid, niacin, nicotinamide or inositol hexanicotinate (inositol hexaniacinate), vitamin B9, more particularly in its form of folic acid or folates, more particularly in their form of pteroylmonoglutamic acid, calcium L-methylfolate or (6S)-5-methyltetrahydrofolic acid in the form of glucosamine salt, vitamin H2, B7 or BW, more particularly in its form of biotin, choline, more particularly in its form of choline chloride, choline dihydrogen citrate or choline bitartrate, inositol, carnitine, more particularly in its form of L-carnitine or L-carnitine L-tartrate, or taurine.

As examples of prebiotics optionally present in the food supplement which is a subject of the present invention, mention may be made of inulin, transgalactooligosaccharides, fructans and mannooligosaccharides.

As examples of probiotics optionally present in the food supplement which is a subject of the present invention, mention may be made of various strains of *Saccharomyces cerevisiae*, of *Bacillus cereus* var. *toyoi*, of *Bacillus subtilis*, alone or in combination with *Bacillus licheniformis*, or also strains of *Enteroccocus faecium*.

These strains of microorganisms are generally combined with a solid support, for example calcium carbonate, dextrose or sorbitol.

As examples of proteins and/or protein concentrates optionally present in the food supplement which is a subject of the present invention, mention may be made of milk proteins resulting from milk cracking, such as colostrum in the form of a lyophilized or atomized powder, whey in the form of a powder, of fractions which are purified or enriched in IgG, in lactoferrin or in lactoperoxidase.

As examples of plant or animal enzymes optionally present in the food supplement which is a subject of the present invention, mention may be made of Promutase, superoxide dismutase (SOD), 3-phytase, 6-phytase, endo-1,4-β-glucanases, endo-1,4-β-xylanases, or also other enzymes which improve or promote digestion.

As examples of peptides optionally present in the food supplement which is a subject of the present invention, mention may be made of avocado peptides, lupin peptides, *quinoa* peptides, maca peptides, fermented or unfermented soybean peptides, rice peptides, peptides present in *Acacia macrostachya* seed extract or peptides present in passionflower seed extracts.

As examples of amino acids optionally present in the food supplement which is a subject of the present invention, mention may be made of alanine, arginine, asparagine, aspartic acid, cysteine, glutamic acid, glutamine, glycine, histidine, isoleucine, leucine, lysine, methionine, phenylalanine, proline, hydroxyproline, pyrrolysine, selenocysteine, serine, threonine, tryptophan, tyrosine, valine, sarcosine or ornithine.

As examples of sugars optionally present in the food supplement which is a subject of the present invention, mention may be made of water-soluble polysaccharides, or sugars of lower molecular weight, such as oligosaccharides or mono- or disaccharides, such as, for example, glucose, lactose or dextrose.

As examples of flavor enhancers optionally present in the food supplement which is a subject of the present invention, mention may be made of glutamates, such as, for example, glutamic acid, monosodium glutamate, monopotassium glutamate, calcium diglutamate, ammonium glutamate or magnesium diglutamate; guanylates, such as, for example, guanylic acid (guanosine monophosphate), disodium guanylate, dipotassium guanylate or calcium guanylate, inosinates, such as, for example, inosinic acid, disodium inosinate, dipotassium inosinate or calcium inosinate, or also intense sweeteners, such as *Stevia* extracts or rebaudiosides.

Lastly, the present invention also provides:
- an oil from seeds of at least one umbelliferous plant as defined previously for use in a therapeutic treatment intended to prevent or slow the appearance of dysesthetic sensations on sensitive human skin;
- an edible composition ($C_A$) as defined previously for use in a therapeutic treatment intended to prevent or slow the appearance of dysesthetic sensations on sensitive human skin;
- a food supplement as defined previously for use in a therapeutic treatment intended to prevent or slow the appearance of dysesthetic sensations on sensitive human skin.

BIBLIOGRAPHY (1): "Definition of Sensitive Skin: An Expert Position Paper from the Special Interest Group on Sensitive Skin of the International Forum for the Study of Itch". Misery, Ständer, Szepietowski, Reich, Wallengren, Evers, Takamori, Brenaut, Le Gall-Ianotto, Fluhr, Berardesca, Weisshaar. Acta Derm Venereol. 2017 Jan. 4; 97(1):4-6)

(2): "Sensitive skin". Misery, Loser, Ständer. J Eur Acad Dermatol Venereol. 2016 February; 30 Suppl 1:2-8

(3): "Putative neuronal mechanisms of sensitive skin." Ständer, Schneider, Weishaupt, Luger, Misery. Exp Dermatol. 2009 May; 18(5):417-23.

(4): "TRPV1 and TRPA1 in cutaneous neurogenic and chronic inflammation: pro-inflammatory response induced by their activation and their sensitization." Gouin, L'Herondelle, Lebonvallet, Le Gall-Ianotto, Sakka, Buhé, Plée-Gautier, Carré, Lefeuvre, Misery, Le Garrec. Protein Cell. 2017 September; 8(9):644-661

(5): "Regulation of Pain and Itch by TRP Channels". Moore, Gupta, Jordt, Chen, Liedtke. Neurosci Bull. 2018 February; 34(1):120-142

(6): "Mediators of Chronic Pruritus in Atopic Dermatitis: Getting the Itch Out?" Mollanazar N K, Smith P K, Yosipovitch G. Clin Rev Allergy Immunol. 2016 December; 51(3):263-292

(7): Yadav & Chaudhary. "Cosmeceutical assets of ancient and contemporary ayurvedic astuteness". Int J Green Phar 2015, 9: S1-S6

(8): Coriander (*Coriandrum sativum*): "A promising functional food toward the well-being". Prachayasittikul, Prachayasittikul, Ruchirawat. Food Res Int 2018. 105: 305-323.

(9): "Anti-inflammatory potential of a lipolotion containing coriander oil in the ultraviolet erythema test." Reuter, Huyke, Casetti, Theek, Frank, Augustin, Schempp. J Dtsch Dermatol Ges. 2008 October; 6(10):847-51.

(10): "Study of The Anti-Inflammatory Activity of Some Medicinal Edible Plants Growing in Egypt." Ammar, Al-Okbi, Mohamed. Med J Islamic World Acad Sci. 1997; 10(4): 113-122

(11): "Characterization of antiradical and anti-inflammatory activities of some cold pressed oils in carrageenan-induced rat model of acute inflammation. Attia, Ibrahim, Maklad, Ahmed, Ramadan. Der Pharma Chemica, 2016, 8(17):148-158"

(12): "Biochemical characterization, anti-inflammatory properties and ulcerogenic traits of some cold-pressed oils in experimental animals". Ibrahim, Attia, Maklad, Ahmed, Ramadan. Pharm Biol. 2017 December; 55(1): 740-748), (13): "Evaluation of coriander spice as a functional food by using in vitro bioassays." Zhang, Dissanayake, Kevseroglu, Nair. Food Chemistry 2015, 167: 24-29

The following example illustrates the invention without, however, limiting it.

The in vitro example described here relates to the reduction in the activation of the receptor TRPA1, involved in the induction of sensations of itching/irritation/scratching/pain of the skin following certain stimulations.

Protection Against Activation of TRPA1 (Neuron Experts Service)

Principle of the Method

Human sensory neurons were obtained from pluripotent stem cells and cultured in culture plates. Human keratinocytes were grown and then seeded above the neurons.

After 19 days of co-culture at 37° C. in a humid atmosphere under 5% CO2, the test products or the positive reference, HC030031 (C18H21N5O3), at 10 µM, and also the fluorescent probe Fluo-4 AM, were added to the co-culture. The Fluo-4 AM probe makes it possible to follow the rapid kinetics of the variation of the intracellular calcium concentration by measuring in real time its fluorescence intensity, and the calcium flux is associated with activation of TRPA1.

After 30 minutes of incubation, the culture medium was removed and the cultures were washed and then reincubated with the test products. Immediately afterwards, they were placed under an inverted microscope and observed in epifluorescence. The cells were observed for 3 minutes, a photograph being taken around every 333 ms. Five seconds after starting the recording, the neurons were stimulated with 10-3 M AITC (allyl isothiocyanate).

Statistical Elements:

The experiments were carried out in 6 replicates. The fluorescence was analyzed for 3 minutes.

The fluorescence values were expressed as means+/−sem [standard error of the mean=standard deviation/root (number of values)].

For each condition, the percentages of stimulation and of protection were calculated as follows:

% stimulation=100×[mean(condition)]/[mean(cells stimulated with AITC)]

% protection=100×[mean(condition)−mean(cells stimulated with AITC)]/[mean(unstressed cells)−mean(cells stimulated with AITC)].

Statistical analysis was performed by a one-way ANOVA test with a significance threshold set at 5%, by comparing the conditions in pairs. A difference between the efficacy of two products was considered:
significant if p<0.05;
"at the limit of significance" if 0.05≤p<0.1;
and not significant if p>0.1.
Results

TABLE

Activation of TRPA1 following stimulation with AITC.

| | AU Mean +/− sem | % stimulation | % protection |
|---|---|---|---|
| Untreated cells (control) | 4968 +/− 72 | 15% | 100% |
| 1 mM AITC | 34035 +/− 1910*** | 100% | 0% |
| +10 µM HC030031 (positive reference) | 8537 +/− 553*** | 25% | 88% |
| +0.001% coriander seed oil | 16337 +/− 871*** | 48% | 61% |

***p < 0.001

AITC induced a significant increase in the activation of TRPA1 (585% vs non-stimulated cells) in the keratinocyte-neuron co-culture.

HC30031, a TRPA1 antagonist, significantly reduced the activation of TRPA1 by 88%. 0.001% coriander seed oil also made it possible to significantly reduce the activation of TRPA1, by 61%.

CONCLUSION

Coriander seed oil is able to reduce the activation of TRPA1 in a human keratinocyte-neuron co-culture model.

The invention claimed is:

1. An edible composition ($C_A$) comprising, per 100% of its weight:
from 1% to 90% of at least one oil from coriander seeds, in ingestible form for slowing the appearance of dysesthetic sensations on sensitive human skin, said at least one oil comprising, per 100% of its weight, a proportion of greater than or equal to 99%, of at least one triglyceride of formula (I):

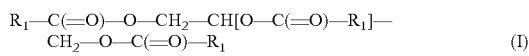

$R_1$—C(=O)—O—CH$_2$—CH[O—C(=O)—$R_1$]—CH$_2$—O—C(=O)—$R_1$  (I)

wherein $R_1$—C(=O)— is an acyl radical selected from members of the group consisting of the radicals palmitoyl (or hexadecanoyl), stearoyl (or octadecanoyl), petroselinoyl (or (Z)-octadec-6-enoyl), oleyl (or cis-octadec-9-enoyl), and linoleoyl (or cis, cis-9,12-octadecadienoyl), linolenoyl (or (9Z,12Z,15Z)-9,12,15-octadecatrienoyl) and comprising per 100% of the weight of the at least one triglyceride of formula (I), an amount by weight of between 60% and 75%, of a triglyceride of formula (I) for which the radical R1C(=O)— is the petroselinoyl (or (Z)-octadec-6-enoyl) radical, and
from 10% to 99% of at least one edible technological additive.

2. The composition as claimed in claim 1, characterized in that the edible technological additive is a diluent, a flow agent, a binder or a disintegrating agent.

3. The composition as claimed in claim 2, characterized in that the diluent is chosen from lactose, sucrose, saccharose, glucose, maltodextrin, mannitol, sorbitol, xylitol, isomalt, calcium hydrogen phosphate, microcrystalline cellulose, starches and more particularly corn starches, wheat starches, potato starches, dicalcium phosphate, anhydrous dibasic calcium phosphate, sodium carbonate, calcium carbonate and magnesium carbonate, monoglycerides and/or diglycerides of fatty acids comprising from 8 to 24 carbon atoms.

4. The composition as claimed in claim 2, characterized in that the flow agent is chosen from magnesium stearate, talc, sodium stearyl fumarate, hydrogenated vegetable oils, anhydrous colloidal silica, sodium benzoate and silica dioxide.

5. The composition as claimed in claim 2, characterized in that the binder is chosen from starches in the form of starch paste, pregelatinized starches, hydroxypropyl methyl cellulose, methyl cellulose, sucrose syrups and acacia gum.

6. The composition as claimed in claim 2, characterized in that the disintegrating agent is chosen from starches, sodium starch glycolate, alginic acid, sodium alginate, sodium croscarmellose, crospovidone, polyvinylpyrrolidone.

7. A food supplement making it possible to slow the appearance of dysesthetic sensations on sensitive human skin and comprising an edible composition ($C_A$) as claimed in claim 2.

8. The food supplement as claimed in claim 7, characterized in that it is in solid or liquid form.

9. The food supplement as claimed in claim 8, characterized in that it is in solid form and takes the form of a tablet, a hard capsule, a soft capsule, a powder, a sugar-coated tablet or granules.

10. The food supplement as claimed in claim 7, characterized in that it comprises, per 100% of its weight, from 5% to 70% by weight, more particularly from 10% to 70% by weight, and more particularly still from 25% to 70% by weight, of the edible composition ($C_A$).

11. The food supplement as claimed in claim 7, characterized in that it comprises at least one active principle chosen from bioactive lipids, water-soluble or water-dispersible trace element salts, water-soluble or liposoluble vitamins, prebiotics, probiotics, milk proteins and/or milk protein concentrates, plant or animal enzymes, amino acids, peptides, sugars, flavor enhancers and flavoring agents.

12. A food supplement as defined in claim 7 for use in a therapeutic treatment intended to slow the appearance of dysesthetic sensations on sensitive human skin.

13. An edible composition ($C_A$) as defined in claim 1 for use in a therapeutic treatment intended to slow the appearance of dysesthetic sensations on sensitive human skin.

* * * * *